United States Patent [19]

Schmidt

[11] 4,134,879

[45] Jan. 16, 1979

[54] THIOETHER-CONTAINING PHENOLIC ANTIOXIDANT STABILIZED POLYMERS

[75] Inventor: Andreas Schmidt, Reinach, Switzerland

[73] Assignee: Ciba-Geigy Corporation, Ardsley, N.Y.

[21] Appl. No.: 739,179

[22] Filed: Nov. 5, 1976

[51] Int. Cl.² .............................................. C08K 5/13
[52] U.S. Cl. ............................ 260/45.85 P; 568/592; 260/45.8 A; 260/45.8 RW; 260/338; 260/340.6; 260/340.7; 260/340.9 R; 260/327 C; 260/327 M; 260/327 P; 260/600 R; 560/8; 560/75; 560/15; 260/609 F; 562/426
[58] Field of Search ............. 260/45.85 P, 470, 473 R, 260/516, 592 R, 600 R

[56] References Cited

U.S. PATENT DOCUMENTS

| | | | |
|---|---|---|---|
| 3,699,152 | 10/1972 | Hechenbleikner et al. | ... 260/45.85 P |
| 3,721,704 | 3/1973 | Dexter | ............................ 260/45.85 P |
| 3,847,994 | 11/1974 | Creger et al. | ......................... 260/600 |
| 3,948,946 | 4/1976 | Hofer et al. | ........................ 260/340.7 |

*Primary Examiner*—V.P. Hoke
*Attorney, Agent, or Firm*—Vincent J. Cavalieri

[57] ABSTRACT

Compounds of the general formula I

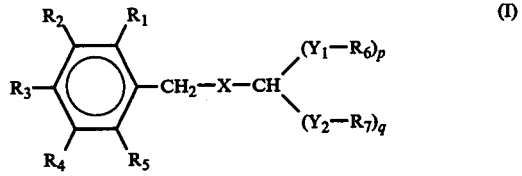

in which $R_1$ and $R_5$ independently of one another denote hydrogen or lower alkyl, one of $R_2$ and $R_3$ denotes hydroxyl and the other denotes alkyl, cycloalkyl or aralkyl, $R_4$ denotes hydrogen or, if $R_3$ denotes hydroxyl, additionally also denotes alkyl, cycloalkyl or aralkyl, X denotes a group

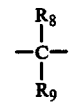

wherein $R_8$ is alkyl, aralkyl or phenyl and $R_9$ is alkyl, aralkyl, phenyl or the group

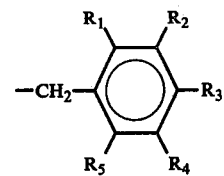

or $R_9$ and $R_8$ together are alkylene, $Y_1$ and $Y_2$ independently of one another denote oxygen or sulphur, p denotes 1 or 2, q denotes 0 or 1, with the proviso that p + q = 2, and $R_6$, if q is 0, denotes alkyl, cycloalkyl, aralkyl or thiaalkyl, in which case $Y_1$ is linked to a carbon atom in the thiaalkyl radical which does not carry a further hetero-atom, or denotes oxaalkyl, in which case $Y_1$ is linked to a carbon atom in the oxaalkyl radical which does not carry a further hetero-atom, hydroxycarbonylalkyl, alkoxycarbonylalkyl, cycloalkoxycarbonylalkyl, aralkoxycarbonylalkyl, aryloxycarbonylalkyl or a group

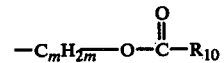

wherein m is 2 – 10 and $R_{10}$ is alkyl, alkenyl, cycloalkyl, aralkyl, thiaalkyl, oxaalkyl or aryl, or $R_6$, if q is 0, and $Y_1$ and $Y_2$ both denote sulphur, can also denote aryl, or $R_6$, if q is 1, denotes, together with $R_7$, 1,2-alkylene, 1,3-alkylene, o-arylene or 1,8-naphthylene, are used to stabilize organic material.

10 Claims, No Drawings

THIOETHER-CONTAINING PHENOLIC ANTIOXIDANT STABILIZED POLYMERS

This is a continuation of application Ser. No. 542,632 filed on Jan. 20, 1975 now abandoned.

The invention relates to new phenol-acetals, processes for their manufacture, their use for the protection of substrates which are sensitive to oxidation, and, as an industrial product, the substrates which are protected with their aid.

It is known, for example, from German Patent Specification No. 1,201,349, to employ derivatives of sterically hindered phenols as stabilisers for organic materials, such as polymers, against thermo-oxidative degradation thereof or against aging thereof by light. It is also known, from DOS No. 2,059,916 to use acetals and thioacetals of alkylated p-hydroxybenzaldehydes. However, the stabilising action of this last-named class of compounds is inadequate. On the other hand, many phenol derivatives exhibit the disadvantage that they objectionably discolour the organic material to be protected, either already when being incorporated or when exposed to light or when they are in contact with industrial waste gases or when they are in contact with hot water, which greatly limits their industrial applicability. Surprisingly, new compounds have been found which far exceed in effectiveness the known derivatives of p-hydroxybenzaldehyde and which are distinguished by significantly better colour stability even at elevated temperatures.

The new compounds correspond to the general formula I

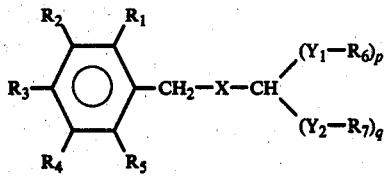

(I)

in which $R_1$ and $R_5$ independently of one another denote hydrogen or lower alkyl, one of $R_2$ and $R_3$ denotes hydroxyl and the other denotes alkyl, cycloalkyl or aralkyl, $R_4$ denotes hydrogen or, if $R_3$ denotes hydroxyl, additionally also denotes alkyl, cycloalkyl or aralkyl, X denotes a group

wherein $R_8$ is alkyl, aralkyl or phenyl and $R_9$ is alkyl, aralkyl, phenyl or the group

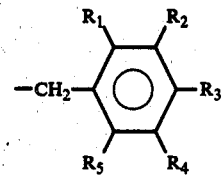

or $R_9$ and $R_8$ together are alkylene, $Y_1$ and $Y_2$ independently of one another denote oxygen or sulphur, p denotes 1 or 2, q denotes 0 or 1, with the proviso that p + q = 2, and $R_6$, if q is 0, denotes alkyl, cycloalkyl, aralkyl or thiaalkyl, in which case $Y_1$ is linked to a carbon atom in the thiaalkyl radical which does not carry a further hetero-atom, or denotes oxaalkyl, in which case $Y_1$ is linked to a carbon atom in the oxaalkyl radical which does not carry a further hetero-atom, hydroxycarbonylalkyl, alkoxycarbonylalkyl, cycloalkoxycarbonylalkyl, aralkoxycarbonylalkyl, aryloxycarbonylalkyl or a group

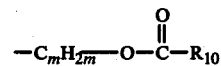

wherein m is 2 – 10 and $R_{10}$ is alkyl, alkenyl, cycloalkyl, aralkyl, thiaalkyl, oxaalkyl or aryl, or $R_6$, if q is 0, and $Y_1$ and $Y_2$ both denote sulphur, can also denote aryl, or $R_6$, if q is 1, denotes, together with $R_7$, 1,2-alkylene, 1,3-alkylene, o-arylene or 1,8-naphthylene.

Preferred compounds of the formula I are those in which $R_1$ and $R_5$ independently of one another denote hydrogen or methyl, one of $R_2$ and $R_3$ denotes hydroxyl and the other denotes alkyl having 1 – 8 carbon atoms, cycloalkyl having 6 – 8 carbon atoms or aralkyl having 7 – 9 carbon atoms, $R_4$ denotes hydrogen or, if $R_3$ denotes hydroxyl, additionally also denotes alkyl having 1 – 8 carbon atoms, cycloalkyl having 6 – 8 carbon atoms or aralkyl having 7 – 9 carbon atoms, X denotes a group

wherein $R_8$ is alkyl having 1-8 carbon atoms, aralkyl having 7-9 carbon atoms, or phenyl, and $R_9$ is alkyl having 1-8 carbon atoms, aralkyl having 7-9 carbon atoms, phenyl or the group

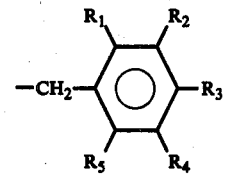

or, conjointly with $R_8$, is alkylene having 2 – 11 carbon atoms, $Y_1$ and $Y_2$ independently of one another denote oxygen or sulphur, p denotes 1 or 2, q denotes 0 or 1, with the proviso that p + q = 2, and $R_6$, if q is 0, denotes alkyl having 1 – 18 carbon atoms, cycloalkyl having 5 – 8 carbon atoms, aralkyl having 7 – 9 carbon atoms, thiaalkyl having 3 – 20 carbon atoms, $Y_1$ being bonded to a carbon atom in the thiaalkyl radical which does not carry a further hetero-atom, oxaalkyl having 3 – 20 carbon atoms, $Y_1$ being bonded to a carbon atom in the oxaalkyl radical which does not carry a further heteroatom, hydroxycarbonylalkyl having 2 – 20 carbon atoms, alkoxycarbonylalkyl having 3 – 20 carbon atoms, cycloalkoxycarbonylalkyl having 7 – 10 carbon atoms, aralkoxycarbonylalkyl having 9 – 13 carbon atoms, phenoxycarbonylalkyl having 8 – 12 carbon atoms, alkylphenoxycarbonylalkyl having 9 – 16 carbon atoms, dialkylphenoxycarbonylalkyl having 10 – 16 carbon atoms, chlorophenoxycarbonylalkyl having 8 – 12 carbon atoms, dichlorophenoxycarbonylalkyl having 8 – 12 carbon atoms or a group

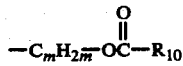

wherein m is 2 – 10 and $R_{10}$ is alkyl having 1 – 17 carbon atoms, alkenyl having 2 – 17 carbon atoms, cycloalkyl having 5 – 8 carbon atoms, aralkyl having 7 – 9 carbon atoms, thiaalkyl having 2 – 20 carbon atoms, oxaalkyl having 2 – 20 carbon atoms, phenyl, alkylphenyl having 7 – 14 carbon atoms, dialkylphenyl having 8 – 14 carbon atoms, alkoxyphenyl having 7 – 14 carbon atoms or chlorophenyl, or $R_6$, if q is 0, and $Y_1$ and $Y_2$ both denote sulphur, also denotes phenyl or alkylphenyl having 7 – 14 carbon atoms, or $R_6$, if q is 1, together with $R_7$ denotes 1,2-alkylene having 2 – 8 carbon atoms, 1,3-alkylene having 3 – 8 carbon atoms, or o-phenylene.

Particularly preferred compounds are those of the formula Ia

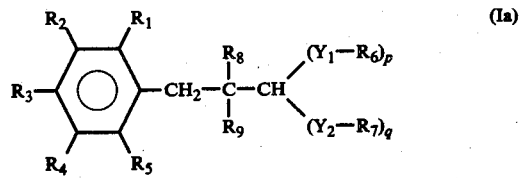

in which $R_1$ and $R_5$ independently of one another denote hydrogen or methyl, one of $R_2$ and $R_3$ denotes hydroxyl and the other denotes alkyl having 1 – 4 carbon atoms, $R_4$ denotes hydrogen or, if $R_3$ denotes hydroxyl, additionally also denotes alkyl having 1 – 4 carbon atoms, $R_8$ denotes alkyl having 1 – 4 carbon atoms or phenyl, $R_9$ denotes alkyl having 1 – 4 carbon atoms, phenyl or the group

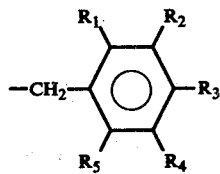

or together with $R_8$ denotes alkylene having 4 or 5 carbon atoms, $Y_1$ and $Y_2$ independently of one another denote oxygen or sulphur, p denotes 1 or 2, q denotes 0 or 1 with the proviso that p + q = 2, and $R_6$, if q is 0, denotes alkyl having 1 – 18 carbon atoms, cycloalkyl having 5 – 6 carbon atoms, benzyl or alkoxycarbonylalkyl having 3 – 20 carbon atoms, or, if q is 1, denotes, together with $R_7$, ethylene, trimethylene, 1-methyltrimethylene, 2,2-dimethyltrimethylene or o-phenylene.

Amongst the particularly preferred compounds there should above all be mentioned compounds of the formula Ib

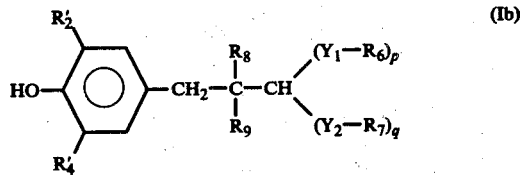

in which $R_2'$ denotes alkyl having 1 – 4 carbon atoms, $R_4'$ denotes alkyl having 3 – 4 carbon atoms, $R_8$ denotes alkyl having 1 – 4 carbon atoms, $R_9$ denotes alkyl having 1 – 4 carbon atoms or together with $R_8$ denotes pentamethylene, $Y_1$ and $Y_2$ independently of one another denote oxygen or sulphur, p denotes 1 or 2, q denotes 0 or 1 with the proviso that p + q is 2, and $R_6$, if q is 0, denotes alkyl having 1 – 18 carbon atoms, benzyl or alkoxycarbonylalkyl having 3 – 20 carbon atoms or, if q is 1, denotes, together with $R_7$, ethylene, trimethylene or 2,2-dimethyltrimethylene.

In the definition of the compounds of the formula I, $R_1$ and $R_5$ can be lower alkyl. This can be lower alkyl having 1 to 6 carbon atoms, such as methyl, ethyl, n-propyl, n-butyl, n-amyl or hexyl.

If $R_2$, $R_3$, $R_4$, $R_6$, $R_8$, $R_9$ and/or $R_{10}$ denote alkyl, they are, for example, methyl, ethyl, iso-propyl, n-butyl, sec.-butyl, tert.-butyl, n-amyl, tert.-amyl, sec.-amyl, hexyl, octyl, tert.-octyl, decyl, dodecyl, tetradecyl or octadecyl.

$R_2$, $R_3$, $R_4$, $R_6$ and/or $R_{10}$ can denote cycloalkyl groups, such as cyclopentyl, cyclohexyl, α-methylcyclohexyl or cyclooctyl $R_2$, $R_3$, $R_4$, $R_6$, $R_8$, $R_9$ and/or $R_{10}$ can be aralkyl groups, such as benzyl, α-phenylethyl or α,α-dimethylbenzyl.

$R_6$ together with $R_7$ and/or $R_8$ together with $R_9$ also denote alkylene, such as ethylene, trimethylene, tetramethylene, pentamethylene, 1-methyltetramethylene or 2,2-dimethyltrimethylene.

When $R_6$ and/or $R_{10}$ denote thiaalkyl they can be, for example, 3-thiabutyl, 3-thiapentyl, 3-thiaheptyl, 3-thiaundecyl, 3-thiapentadecyl, 3-thianonadecyl or 3-thiaheneicosyl, whilst when they denote oxaalkyl they can be 3-oxabutyl, 2-oxapentyl, 2-oxaheptyl, 3-oxapentadecyl or 2-oxaheneicosyl.

When $R_6$ and/or $R_{10}$ denote aryl they can be, for example, phenyl, 4-tert.butylphenyl, α-naphthyl or β-naphthyl.

$R_6$ can also denote hydroxycarbonylalkyl such as hydroxycarbonylmethyl, hydroxycarbonylethyl or hydroxycarbonylpropyl, alkoxycarbonylalkyl, such as methoxycarbonylmethyl, ethoxycarbonylmethyl, octoxycarbonylmethyl, octoxycarbonylethyl, decyloxycarbonylmethyl or octadecyloxycarbonylmethyl, cycloalkoxycarbonylalkyl, such as cyclohexyloxycarbonylmethyl, aralkoxylcarbonylakyl, such as benzyloxycarbonylmethyl, or substituted or unsubstituted aryloxycarbonylalkyl, such as phenoxycarbonylmethyl or chlorophenoxycarbonylmethyl.

When $R_{10}$ denotes alkenyl it can be vinyl, propenyl or butenyl.

Examples of compounds of the formula (I) are: 5-[1,1-dimethyl-2-(3-tert.butyl-4-hydroxy-5-methylphenyl)ethyl]-4,6-di-thiaazelaic acid dioctadecyl ester, 10-[1,1-dimethyl-2- (3-tert.butyl-4-hydroxy-5,6-dimethylphenylethyl]-9,11-dithianonadecane, 2-[1,1-dimethyl-2-(2,6-dimethyl-3-hydroxy-4-tert.butyl-phenyl)ethyl]-1,3,-dithiane, 2-[1,1-dimethyl-2-(3,5-dicyclooctyl-4-hydroxyphenyl)ethyl]-1,3-oxathiolane, 4-[1,1-dimethyl-2-(3-tert.butyl-4-hydroxy-5-methylphenyl)ethyl]-3,5-dithiapimelic acid dioctadecyl ester, 4-[1,1dimethyl-2-(3,5di-isopropyl-4-hydroxyphenyl)ethyl]-3,5-dithiapimelic acid dioctadecyl ester, 4-[1,1-dimethyl-2(3,5-dimethyl-4-hydroxyphenyl)ethyl]-3,5-dithiapimelic acid dioctadecyl ester, 4-[1,1-dimethyl-2-(3,5-ditert.butyl-4-hydroxyphenyl)ethyl]3,5-dithiapimelic acid dioctadecyl ester, 2-[1,1-dimethyl-2-(3,5-di-tert.butyl-4-hydroxyphenyl)ethyl]-1,3dithiolane, 2-[1,1-dimethyl-2-(3,5-di-tert.butyl-4-hydroxyphenyl) ethyl]-1,3-dioxolane, 13-]1,1-dimethyl-2-(3,5-di-(1-methylcyclohexyl)-4-hydroxyphenyl)ethyl]-9,17-dithia-12,14-dioxapentaconsane and 3-]1,1-dimethyl-2-(2,6-dimethyl-3-hydroxy-4-(1-methylcyclohexyl)phenyl)-ethyl]-1,5-diphenyl-2,4-dithiapentane.

The compounds of the formula I are manufactured, if q is 0, by reacting one mol of a compound of the formula II

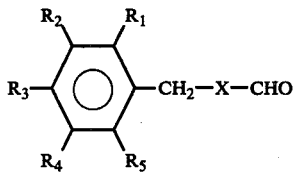

with 2 mols of a compound of the formula III

of, if q is 1, with one mol of a glycol, a monothioglycol, a dithioglycol, an o-dihydroxyarylene, an o-dimercaptoarylene or an o-hydrocymercaptoarylene, such as, for example, one of the compounds of the formulae IV or V

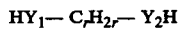

wherein r is 2 to 8, or

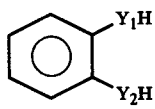

or with one mol of a compound of the formula VI

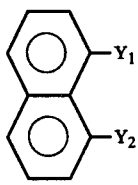

wherein $Y_1$ and $Y_2$ independently of one another denote oxygen or sulphur.

The reaction is carried out in a solvent in the presence of an acid catalyst. Examples of possible solvents are: aromatic hydrocarbons such as benzene, toluene or xylene, aliphatic hydrocarbons such as hexane, cyclohexane, heptane, octane or ligroin, ketones such as acetone, methyl ethyl ketone and cyclohexanone, alcohols such as methanol, ethanol, isopropanol, butanol and cyclohexanol, ethers such as diethyl ether, dioxane and tetrahydrofurane, esters such as ethyl acetate and amyl acetate, and the like.

Solvents which are used preferentially are those which are suitable for azeotropic distillation of the water split off during the reaction, such as, for example, benzene, toluene, xylene, n-propanol, isopropanol, methyl ethyl ketone, ethyl acetate, n-butanol, dioxane, n-hexane and cyclohexane.

The water formed can also be removed with the aid of an inert drying agent added during the reaction, such as, for example, calcium chloride, sodium sulphate and the like.

The acid catalyst is employed in a concentration of 0.1–10 mol %, preferably 0.5–5 mol %, and particularly preferentially 1–3 mol %, calculated relative to the aldehyde of the formula II. Examples of catalysts which can be used are: anhydrous hydrochloric acid, sulphuric acid, orthophosphoric aicd, pyrophosphoric acid, chloroacetic acid, benzenesulphonic acid, p-bromosulphonic acid and p-toluenesulphonic acid.

If the water split off is distilled off azeotropically, the temperature at which the reaction is carried out is determined by the boiling point of the solvent used or of its azeotrope with water; preferably, the reaction is carried out in solvents of boiling point between 70 and 140° C. If the water split off is removed by a drying agent, temperatures of 0° C to 150° C, preferably 20° C to 70° C, are used.

The starting materials of the formulae II to VI are known or can be prepared by known processes.

Organic materials such as, for example, the following polymers, can be stabilised using the compounds of the formula I.

1. Polymers which are derived from hydrocarbons with single or double unsaturation, such as polyolefines, for example, polyethylene, which can optionally be crosslinked, polypropylene, polyisobutylene, polymethylbutene-1, polymethylpentene-1,polybutene-1, polyisoprene, polybutadiene, polystyrene, polyisobutylene, copolymers of the monomers on which the homopolymers mentioned are based, such as ethylenepropylene copolymers, propylene-butene-1 copolymers, propylene-isobutylene copolymers, styrene-butadiene copolymers and terpolymers of ethylene and propylene with a diene, such as, for example, hexadiene, dicyclopentadiene or ethylidenenorbornene; mixtures of the above-mentioned homopolymers, such as, for example, mixtures of polypropylene and polyethylene, polypropylene and polybutene-1, or polypropylene and polyisobutylene.

2. Vinyl polymers containing halogen, such as polyvinyl chloride, polyvinylidene chloride, polyvinyl fluoride, but also polychloroprene and chlorinated rubbers.

3. Polymers which are derived from $\alpha,\beta$-unsaturated acids and their derivatives, such as polyacrylates and polymethacrylates, polyacrylamides and polyacrylonitrile, as well as their copolymers with other vinyl compounds, such as acrylonitrile/butadiene/styrene, acrylonitrile/styrene and acrylonitrile/styrene/acrylic ester copolymers.

4. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate, polyallyl melamine and their copolymers with other vinyl compounds, such as ethylene/vinyl acetate copolymers.

5. Homopolymers and copolymers which are derived from epoxides, such as polyethylene oxide or the polymers which are derived from bis-glycidyl ethers.

6. Polyacetals, such as polyoxymethylene and polyoxyethylene, as well as those polyoxymethylenes which contain ethylene oxide as the comonomer.

7. Polyphenylene oxides.
8. Polyurethanes and polyureas.
9. Polycarbonates.
10. Polysulphones.
11. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.

12. Polyesters which are derived from dicarboxylic acids and diacohols and/or from hydroxycarboxylic acids or the corresponding lactones, such as polyethylene glycol terephthalate or poly-1,4-dimethylolcyclohexane terephthalate.

13. Crosslinked polymers which are derived from aldehydes on the one hand and phenols, ureas and melamines on the other, such as phenol-formaldehyde, urea-formaldehyde and melamine-formaldehyde resins.

14. Alkyd resins, such as glycerine-phthalic acid resins and their mixtures with melamine-formaldehyde resins.

15. Unsaturated polyester resins which are derived from copolyesters of saturated and unsaturated dicarboxylic acids with polyhydric alcohols, with vinyl compounds as crosslinking agents, and also their halogen-containing modifications of low inflammability.

16. Natural polymers such as cellulose, rubber, proteins and their polymer-homologously chemically modified derivatives, such as cellulose acetates, cellulose propionates and cellulose butyrates, or the cellulose ethers, such as methylcellulose.

17. High molecular monomeric substances, for example mineral oils, animal and vegetable fats, oils and waxes, or oils, waxes and fats based on synthetic esters.

The compounds of the formula I are incorporated in the substrates in a concentration of 0.005 to 5% by weight, relative to the material to be stabilised. Preferably, 0.01 to 1.0, particularly preferably 0.02 to 0.5, % by weight of the compounds, relative to the material to be stabilised, are incorporated into the latter. The incorporation can be carried out, for example, by mixing in at least one of the compounds of the formula I and optionally further additives by the methods customary in the art, before or during shaping, or by applying the compounds, dissolved or dispersed, to the polymer, where appropriate with subsequent evaporation of the solvent.

In the case of crosslinked polyethylene, the compounds are added before the crosslinking.

The compounds of the formula I can also be added before or during the polymerisation, it being possible, by a potential incorporation into the polymer chain, to obtain stabilised substrates in which the stabilisers are not volatile or capable of extraction.

The following may be mentioned as examples of further additives with which the compounds of the formula I can be co-employed:

1. Antioxidants 1.1. Simple 2,6-dialkylphenols, such as, for example, 2,6-di-tert.butyl-4-methylphenol, 2-tert.-butyl-4,6-dimethylphenol, 2,6-di-tert.-butyl-4-methoxymethylphenol and 2,6-dioctadecyl-4-methylphenol.

1.2. Derivatives of alkylated hydroquinones, such as, for example, 2,5-di-tert.-butyl-hydroquinone, 2,5-di-tert.-amylhydroquinone, 2,6-di-tert.butyl-hydroquinone, 2,5-di-tert.-butyl-4-hydroxy-anisole, 3,5-di-tert.-butyl-4-hydroxyanisole, tris-(3,5-di-tert.-butyl-4-hydroxyphenyl)-phosphite, 3,5-di-tert.-butyl-4-hydroxyphenyl stearate and bis-(3,5-di-tert.-butyl-4-hydroxyphenyl) adipate.

1.3. Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl)-disulphide.

1.4. Alkylidene-bisphenols, such as, for example, 2,2'-methylene-bis-(6-tert.butyl-4-methylphenol),2,2'-methylene-bis-(6-tert.butyl-4ethylphenol), 4,4'-methylene-bis-(6-tert.-butyl-2-methylphenol), 4,4'-methylene-bis-(2,6-di-tert.-butyl-phenol), 2,6-di-(3tert.butyl-5-methyl-2-hydroxybenzyl)- 4-methylphenol, 2,2'-methylene-bis-[4-methyl-6-(α-methylcyclohexyl)-phenol], 1,1-bis-(3,5-dimethyl-2-hydroxyphenyl)butane, 1,1-bis-(5-tert.butyl-4-hydroxy-2-methylphenyl)-butane, 2,2-bis-(5-tert. -butyl-4-hydroxy-2-methylphenyl)-butane, 2,2-bis-(3,5-di-tert.butyl-4-hydroxyphenyl)-propane, 1,1,3-tris-(5-tert.butyl-4-hydroxy-2-methylphenyl)-butane, 2,2 -bis-(5-tert. butyl-4-hydroxy-2-methylphenyl)-4-n-dodecylmercapto-butane, 1,1,5,5-tetra-(5-tert.butyl)-4-hydroxy-2-methylphenyl)-pentane and ethylene glycol bis-[3,3-bis-(3'-tert.butyl-4'-hydroxyphenyl)-butyrate].

1.5. O-, N- and S-benzyl compounds, such as, for example, 3,5,3',5'-tetra-tert.butyl-4,4'-dihydroxydibenzyl ether, 4-hydroxy-3,5-dimethylbenzyl-mercaptoacetic acid octadecyl ester, tris-(3,5-di-tert.butyl-4-hydroxybenzyl)-amine and bis-(4-tert.butyl-3-hydroxy-2,6-dimethylbenzyl)-dithioterephthalate.

1.6. Hydroxybenzylated malonic esters, such as, for example, 2,2-bis-(3,5-di-tert.butyl-2-hydroxybenzyl)-malonic acid dioctadecyl ester, 2-(3-tert.butyl-4-hydroxy-5-methylbenzyl)-malonic acid dioctadecyl ester, 2,2-bis-(3,5-di-tert.-butyl-4-hydroxybenzyl)-malonic acid didodecylmercaptoethylester and2,2-bis-(3,5-di-tert.butyl-4-hydroxybenzyl)-malonic acid di-[4-(1,1,3,3-tetramethylbutyl)-phenyl]-ester.

1.7. Hydroxybenzyl-aromatics, such as, for example, 1,3,5-tri-(3,5-di-tert.butyl-4-hydroxybenzyl)-2,4,6-trimethylbenzene, 1,4-di-(3,5-di-tert.butyl-4-hydroxybenzyl)-2,3,5,6-tetramethylbenzene and 2,4,6-tri-(3,5-di-tert.butyl-4-hydroxybenzyl)-phenol.

1.8. s-Triazine compounds, such as, for example, 2,4-bis-octylmercapto-6-(3,5-di-tert.butyl-4-hydroxyanilino)-s-triazine, 2-octylmercapto-4,6-bis-(3,5-di-tert.butyl-4-hydroxy-anilino)-s-triazine, 2-octylmercapto-4,6-bis-(3,5di-tert.butyl-4-hydroxy-phenoxy)-s-triazine, 2,4,6-tris-(3,5di-tert.butyl-4-hydroxyphenoxy)-s-triazine, 2,4,6-tris-(3,5-di-tert. butyl-4-hydroxyphenylethyl)-s-triazine and 1,3,5-tris-(3,5-di-tert.butyl-4-hydroxybenzyl)-isocyanurate.

1.9. Amides of β-(3,5-di-tert.butyl-4-hydroxyphenyl)-propionic acid, such as, for example, 1,3,5-tris-(3,5-di-tert.butyl-4-hydroxyphenyl-propionyl)-hexahydro-s-triazine and N,N'-di-(3,5-di-tert.butyl-4-hydroxyphenyl-propionyl)-hexamethylenediamine.

1.10. Esters of β-(3,5-di-tert.butyl-4-hydroxyphenyl)-propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, trishydroxyethyl isocyanurate and 4-hydroxymethyl-1-phospha-2,6,7-trioxabicyclo[2,2,2]octane.

1.11. Esters of β-(5-tert.butyl-4-hydroxy-3-methylphenyl propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2,2,2]octane.

1.12. Esters of 3,5-di-tert.butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, treimethyblpropane, tris-hydroxyethyl isocyanurate and 4-hydroxymethyl-1-phospha-2,6,7-trioxabicyclo[2,2,2]octane.

1.13. Acylaminophenols, such as, for example, N-(3,5-di-tert.-butyl-4-hydroxyphenyl)-stearic acid amide, N,N'-di-(3,5-di-tert.butyl-4-hydroxyphenyl)-thiobis-acetamide and thiophosphoric acid 0,0-diethyl ester 3,5-di-tert.butyl-4-hydroxy anilide.

1.14. Benzylphosphonates, such as, for example, 3,5-di-tert.-butyl-4-hydroxybenzyl-phosphonic acid dimethyl ester, 3,5di-tert.butyl-4-hydroxybenzyl-phosphonic acid diethyl ester, 3,5-di-tert.butyl-and 5-tert.butyl-4-hydroxy-3-methylbenzyl-phosphonic acid dioctadecyl ester.

1.15. Aminoaryl derivatives, such as, for example, phenyl-1-naphthylamine, phenyl-2-naphthylamine, N,N'-dipenyl-p-phenylenediamine N,N'-di-2-naphthyl-p-phenylenediamine, N,N'-di-sec.-butyl-p-phenylenediaine, 6-ethoxy-2,2,4-trimethyl-1,2-dihydroquinoline, 6-dodecyl-2,2,4-trimethyl-1,2-dihydroquinoline, monooctyliminodibenzyl and dioctyliminodibenzyl and polymerised isocyanurate and 4-hydroxymethyl-1-phospha-2,6,7-trioxabicyclo-[2,2,2]octane.

1.12. Esters of 3,5-di-tert.butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2,2,2]octane.

1.13. Acylaminophenols, such as, for example, N-(3,5di-tert.-butyl-4-hydroxyphenyl)-stearic acid amide, N,N'-di-(3,5-di-tert.butyl-4-hydroxyphenyl)-thiobis-acetamide and thiophosphoric acid 0,0-diethyl ester 3,5-di-tert.butyl-4-hydroxy anilide.

1.14. Benzylphosphonates, such as, for example, 3,5-di-tert.-butyl-4-hydroxybenzyl-phosphonic acid dimethyl ester, 3,5di-tert.butyl-4-hydroxybenzyl-phosphonic acid diethyl ester, 3,5-di-tert.butyl-4-hydroxybenzyl-phosphonic acid dioctadecyl ester and 5-tert.butyl-4-hydroxy-3-methylbenzyl-phosphonic acid dioctadecyl ester.

1.15. Aminoaryl derivatives, such as, for example, phenyl-1-naphthylamine, phenyl-2-naphthylamine, N,N'-diphenyl-p-phenylenediamine, N,N'-di-2-naphthyl-p-phenylenediamine, N,N'-di-sec.-butyl-p-phenylediamine, 6-ethoxy-2,2,4-trimethyl-1,2-dihydroquinoline, 6-dodecyl-2,2,4-trimethyl-1,2-dihydroquinoline, monooctyliminodibenzyl and dioctyliminodibenzyl and polymerised 2,2,4-trimethyl-1,2-dihydroquinoline. Octylated diphenylamine, nonylated diphenylamine, N-phenyl-N'-cyclohexyl-p-phenylenediamine, N-phenyl-N'-isopropyl-p-phenylenediamine, N,N'-di-sec.octyl-p-phenylenediamine, N-phenyl-N'-sec.octyl-p-phenylenediamine, N,N'-di-(1,4-dimethylpentyl)-p-phenylenediamine, N,N'-dimethyl-N,N'-di-(sec.octyl)-p-phenylenediamine, 2,6-dimethyl-4-methoxyaniline, 4-ethoxy-N-sec.-butylaniline, the condensation product of diphenylamine and acetone, aldol-1-naphthylamine and phenothiazine.

2. UV absorbers and light stabilisers 2.1. 2-(2'-Hydroxyphenyl)-benztriazoles, such as, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.butyl-, 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert.amyl-, 3'-methyl-5'-carbomethoxyethyl- and 5-chloro-3',5'-di-tert.-amyl-derivative.

2.2. 2,4-Bis-(2'-hydroxyphenyl)-6-alkyl-s-triazines, such as, for example, the 6-ethyl, 6-heptadecyl- or 6-undecyl-derivative.

2.3. 2-Hydroxy-benzophenones, such as, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy-derivative.

2.4. 1,3-Bis-(2'-hydroxy-benzoyl)-benzenes, such as, for example, 1,3-bis-(2'-hydroxy-4'-hexyloxy-benzoyl)-benzene, 1,3-bis-(2'-hydroxy-4'-octyloxy-benzoyl)-benzene and 1,3-bis-(2'-hydroxy-4'-dodecyloxy-benzoyl)-benzene.

2.5. Esters of optionally substituted benzoic acids such as, for example, phenyl salicylate, octylphenyl salicylate, dibenzoylresorcinol, bis-(4-tert.-butylbenzoyl)-resorcinol, benzoyl-resorcinol and 3,5-di-tert.-butyl-4-hydroxybenzoic acid 2,4-di-tert.butyl-phenyl ester, octadecyl ester or 2-methyl-4,6-di-tert.butyl-phenyl ester.

2.6. Acrylates, such as, for example, α-cyano-β,β-diphenyl acrylic acid ethyl ester or isooctyl ester, α-carbomethoxy-cinnamic acid methyl ester, α-cyano-β-methyl-p-methoxy-cinnamic acid methyl ester or butyl ester and N-(β-carbomethoxy-vinyl)-2-methyl-indoline.

2.7. Nickel compounds, such as, for example, nickel complexes of 2,2'-thio-bis-[4-(1,2,3,3-tetramethylbutyl)-phenol], such as the 1:1 or 1:2 complex, optionally with additional ligands such as n-butylamine, triethanolamine or N-cyclohexyl-di-ethanolamine, nickel complexes of bis-[2-hydroxy-4-(1,1,3,3-tetramethylbutyl)-phenyl]-sulphone, such as the 2:1 complex, optionally with additional ligands such as 2-ethyl-caproic acid, nickel dibutyldithiocarbamate, nickel salts of 4-hydroxy-3,5-di-tert.butylbenzyl-phosphonic acid monoalkyl esters, such as of the methyl, ethyl or butyl ester, nickel complexes of ketoximes such as of 2-hydroxy-4-methyl-phenyl undecyl ketonoxime, nickel, 3,5-di-tert.butyl-4-hydroxy-benzoate and nickel isopropyxanthate.

2.8. Sterically hindered amines, such as, for example, 4-benzoyloxy-2,2,6,6-tetramethylpiperidine, 4-stearoyloxy-2,2,6,6-tetramethylpiperidine, bis-(2,2,6,6-tetramethylpiperidyl)-sebacate and 3-n-octyl-7,7,9,9-tetramethyl-1,3,8-triaza-spiro [4,5]decane-2,4-dione.

2.9. Oxalic acid diamides, such as, for example, 4,4'-di-octyl-oxy-oxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis-(3-dimethylaminopropyl)-oxalamide, 2-ethoxy-5-tert.butyl-2'-ethyl-oxanilide and its mixture with 2-ethoxy-2'-ethyl-5,4'-di-tert.butyl-oxanilide and mixtures of orthoand para-methoxy- as well as of o- and p-ethoxy-disubstituted oxanilides.

3. Metal deactivators, such as, for example, oxanilide, isophthalic acid dihydrazide, sebacic acid bis-phenylhydrazide, bis-benzyllidene-oxalic acid dihydrazide, N,N'-diacetyl-adipic acid dihydrazide, N,N'-bis-salicyloyl-oxalic acid dihydrazide, N,N'-bis-salicyloyl-hydrazine, N,N'-bis-(3,5-di-tert.butyl-4-hydroxyphenyl-propionyl)-hydrazine, N-salicylcyl-N'-salicylal-hydrazine, 3-salicyloylamino-1,2,4-triazole and N,N'-bis-salicyloyl-thiopropionic acid dihydrazide.

4. Phosphites, such as, for example, triphenyl phosphite, diphenylalkyl phosphites, phenyldialkyl phosphites, tri-(nonylphenyl) phosphite, trilauryl phosphite, trioctadecyl phosphite, 3,9-di-isodecyloxy-2,4,8,10-tetraoxo-3,9-diphosphaspiro[5,5]-undecane and tri-(4-hydroxy-3,5-di-tert.butylphenyl) phosphite.

5. Compounds which destroy peroxide, such as, for example, esters of β-thiodipropionic acid, for example the lauryl, stearyl, myristyl or tridecyl esters, mercaptobenzimidazole or the zinc salt of 2-mercapto-benzimidazole.

6. Polyamide stablisers, such as, for example, copper salts in combination with iodides and/or phosphorus compounds and salts of divalent manganese. 7. Basic co-stabilisers, such as, for example, melamine, benzoguanamine, polyvinylpyrrolidone, dicyandiamide, trially cyanurate, urea derivatives, hydrazine derivatives, amines, polyamides, polyurethanes, alkali metal salts and alkaline earth metal salts of higher fatty acids, for example Ca stearate, Zn stearate, Mg stearate, Na ricinoleate and K palmitate, antimony pyrocatecholate or zinc pyrocatecholate.

8. PVC stabilisers, such as, for example, organic tin compounds, organic lead compounds and barium-cadmium salts of fatty acids.

9. Nucleating agents, such as, for example, 4-tert.butyl-benzoic acid, adipic acid and diphenylacetic acid.

10. Urea derivatives, such as, for example, N-cyclohexyl-N'-1-naphthyluria, N-phenyl-N,N'-dicyclohexyluria, N-phenyl-N'-2-naphthylurea, N-phenylthiourea and N,N'-dibutylthiourea.

11. Other additives, such as, for example, plasicisers, lubricants, emulsifiers, fillers carbon black, asbestos, kaolin, talc, glass fibres, pigments, optical brighteners, flameproofing agents and antistatic agents.

The invention is described in greater detail in the examples which follow. In these, percentage (%) denotes percentage by weight.

EXAMPLE 1

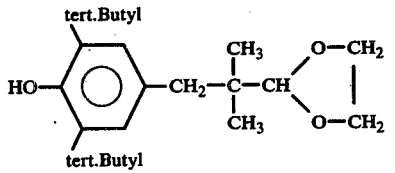

17.4 g (0.06 mol) of 3-(3,5-di-tert.butyl-4-hydroxyphenyl)-2,2-dimethyl-propionaldehyde, 3.7 g (0.06 mol) of ethylene glycol and 0.1g of p-toluenesulphonic acid are dissolved in 100 ml of benzene and heated to the reflux temperature for one hour under a water separator. During this time approx. 1 ml of water separates out. The mixture is then cooled and the benzene solution is washed with water and concentrated to dryness. The oil which remains crystallises on trituration. When recrystallised from methanol, 2-[1,1-dimethyl-2-(3,5-di-tert.butyl-4-hydroxyphenyl)-ethyl]-1,3-dioxolane melts at 73° C (stabiliser No. 1).

If, in this example, the ethylene glycol is replaced by an equimolecular amount of mercaptoethanol, and otherwise the same procedure is followed, 2-[1,1-dimethyl-2-(3,5-di-tert.butyl-4-hydroxyphehyl)-ethyl]-1,3-oxathiolane of melting point 77° C (stabiliser No. 2) is obtained.

If, in this example, he mercaptoethanol is replaced by an equimolecular amount of ethanedithiol and otherwise the same procedure is followed, 2-[1,1-dimethyl-2-(3,5-di-tert.butyl-4-hydroxyphenyl)-ethyl]-1,3-dithiolane of melting point 119° C (stabiliser No. 3) is obtained.

EXAMPLE 2

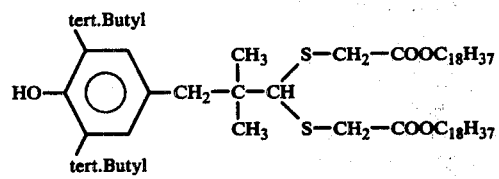

17.4 g (0.06 mol) of 3-(3,5-di-tert.butyl-4-hydroxyphenyl)-2,2-dimethyl-propionaldehyde, 41.4 g (0.12 mol) of thioglycolic acid octadecyl ester and 0.5 g of p-toluenesulphonic acid in 200 ml of benzene and heated under reflux for 2 hours under a water separator. During this time, approx. 1 ml of water separates out. The mixture is then cooled and the benzene solution is washed with water and concentrated to dryness. The oil which remains crystallises on standing. When recrystallised from isopropanol, 4-[1,1-dimethyl-2-(3,3-di-tert.butyl-4-hydroxyphenyl)-ethyl]-3,5-di-thiapimelic acid dioctadecyl ester melts at 60 - 63° C (stabiliser No. 4).

If, in this example, the thioglycolic acid octadecyl ester is replaced by an equivalent amount of the mercaptans of Table 1 below, and otherwise the same procedure is followed, the corresonding dithiocetals of 3-(3,5-ditert.butyl-4-hydroxyphenyl)-2,2-dimethylpropionaldehyde, exhibiting the analytical data indicated, are obtained.

Table 1

| Mercaptan | Analytical results of the diothioacetal | | Stabiliser No. |
|---|---|---|---|
| HS—CH$_2$—COO—CH$_2$—CH(C$_4$H$_9$)(C$_2$H$_5$) | Calculated<br>Found | C 68.79 H 10.07 O 11.72 S 9.40<br>C 69.10 H 10.00 O 11.40 S 9.30 | 5<br>(liquid) |
| HS—CH$_2$—COOC$_2$H$_5$ | Calculated | C 63.30 H 8.63 O 15.59 S 12.50 | 6 |

Table 1-continued

| Mercaptan | Analytical results of the diothioacetal | | Stabiliser No. |
|---|---|---|---|
| | Found | C 63.20 H 8.70 O 15.50 S 12.60 | Melting point: 58–59° C |
| HS—(CH$_2$)$_2$—COOCH$_2$—CH(C$_4$H$_9$)(C$_2$H$_5$) | Calculated<br>Found | C 69.45 H 10.24 O 11.28 S 9.05<br>C 69.70 H 10.30 O 11.00 S 9.00 | 7<br>(liquid) |
| HS—C$_{18}$H$_{37}$ | Calculated<br>Found | C 78.10 H 12.40 O 1.90 S 7.60<br>C 77.80 H 12.60 O 1.50 S 7.80 | 8<br>Melting point: 55–58° C |
| HS—CH$_2$CH$_2$COOH | Calculated<br>Found | C 61.96 H 8.32 O 16.51 S 13.21<br>C 61.72 H 8.17 O 16.74 S 13.22 | 9<br>Melting point: 146° C |
| HS—C$_6$H$_5$ | Calculated<br>Found | C 75.40 H 8.37 O 3.24 S 12.99<br>C 75.51 H 8.25 O 3.13 S 13.11 | 10<br>Melting point: 84° C |

EXAMPLE 3

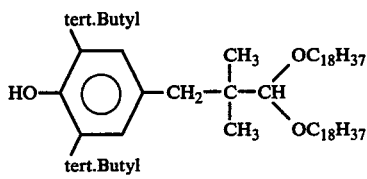

14.5 g (0.05 mol) of 3-(3,5-di-tert.butyl-4-hydroxyphenyl)-2,2-dimethyl-propionaldehyde, 27 g (0.1 mol) of octadecanol and 0.5 g of p-toluenesulphonic acid are dissolved in 150 ml of hot benzene and the solution is heated to the reflux temperature for 90 minutes under a water separator. Thereafter, the benzene solution is cooled, washed with water and completely concentrated. The oily residue is dissolved in a little toluene, unconverted octadecanol which has precipitated is filtered off and the filtrate is purified on a silica gel column with toluene as the running agent. The bis-octadecyl acetal of 3-(3,5-di-tert.butyl-4-hydroxyphenyl)-2,2-dimethyl-propionaldehyde melts at 30 – 35° C. (Stabiliser No. 11)

EXAMPLE 4

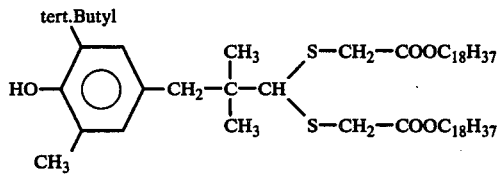

12.4 g (0.05 mol) of 3-(3-tert.butyl-4-hydroxy-5-methylphenyl)-2,2-dimethyl-propionaldehyde, 34.4 g (0.1 mol) of thioglycollic acid octadecyl ester and 0.5 g of p-toluenesulphonic acid in 250 ml of benzene are heated under reflux for two hours under a water separator. During this time, approx. 1 ml of water separates out. Thereafter the benzene solution is cooled, washed with water and concentrated to dryness. The oil which remains solidifies to a wax at room temperature. 4-[1,1-Dimethyl-2-(3-tert.butyl-4-hydroxy-5-methyl-phenyl)-ethyl]-3,5-di-thiapimelic acid dioctadecyl ester (stabiliser No. 12) is thus obtained.

Analysis: Calculated: C, 73.20; H, 11.19; S, 6.98. Found: C, 73.59; H, 11.20; S, 6.89.

If, in this example, 3-(3-tert.butyl-4-hydroxy-5-methylphenyl)-2,2-dimethyl-propionaldehyde is replaced by an equimolecular amount of 3-(4-hydroxy-3,5-di-isopropylphenyl)-2,2-di-methyl-propionaldehyde or 3-(4-hydroxy-3,5-di-methylphenyl)-2,2-dimethyl-propionaldehyde and otherwise the same procedure is followed, 4-[1,1-dimethyl-2-(4-hydroxy-3,5-di-isopropyl-phenyl)-ethyl]-3,5-di-thiapimelic acid dioctadecyl ester (stabiliser No. 13) of melting point 60° C, and 4-[1,1-dimethyl-2-(4-hydroxy-3,5-di-methyl-phenyl)-ethyl]-3,5-thiapimelic acid dioctadecyl ester (stabiliser No. 14) of melting point 40–45° C are obtained, respectively.

EXAMPLE 5

100 parts of polypropylene (melt index 3.2 g/10 minutes, 230° C/2,160 g) are intensively mixed for 10 minutes, in a shaking apparatus, with 0.2 part of an additive listed in Table 2 which follows. The resulting mixture is kneaded in a Brabender plastograph for 10 minutes at 200° C and the composition obtained in this way is then pressed in a platen press at a platen temperature of 260° C to give sheets 1 mm thick, from which strips 1 cm wide and 17 cm long are punched.

The effectiveness of the additives added to the test strips is tested by heat aging in a circulating air oven at 135° and 149° C, an additive-free test strip being used as a comparison. 3 test strips of each formulaion are employed for this purpose. The end point is defined as the incipient, easily visible crumbling of the test strip.

Table 2

| Stabiliser | Days before decomposition begins | |
|---|---|---|
| No. | 149° C | 135° C |
| None | <1 | ~3 |
| 4 | 27 | 79 |
| 5 | 16 | 73 |
| 7 | 5 | 33 |
| 8 | 19 | 88 |
| 12 | 22 | 106 |
| 13 | 20 | 84 |
| 14 | 22 | 112 |

EXAMPLE 6

100 parts of polypropylene (melt index 3.2 g/10 minutes, 230° C/2,160 g) are intensively mixed for 10 minutes, in a shaking apparatus, with 0.1 part of an additive listed in Table 3 which follows and 0.3 part of dilauryl thiodipropionate.

The resulting mixture is kneaded in a Brabender plastograph for 10 minutes at 200° C and the composition obtained in this way is then pressed in a platen press at a platen temperature of 260° C to give sheets 1 mm thick, from which strips 1 cm wide and 17 cm long are punched.

The effectiveness of the additives added to the test strips is tested by heat aging in a circulating air oven at 135° and 149° C, a test strip which only contains 0.3 part of dilauryl thiodipropionate being used as a comparison. Three test strips of each formulation are employed for this purpose. The end point is defined as the incipient, easily visible crumbling of the test strip.

Table 3

| Stabiliser No. | Days before decomposition begins | |
|---|---|---|
| | 149° C | 135° C |
| Comparison | 5 | 11 |
| 4 | 45 | 146 |
| 5 | 23 | 97 |
| 7 | 33 | 99 |
| 8 | 18 | 75 |
| 12 | 96 | 204 |
| 13 | 43 | 99 |
| 14 | 65 | 170 |

EXAMPLE 7

The test pieces described in Example 5 were tested for their colour stability, in particular:
(a) After incorporation (Table 4, column 2)
(b) After 500 hours' exposure in a Xenotest apparatus of Messrs. Hanau (Table 4, column 3)
(c) After treatment with boiling water for 1 week (Table 4, column 4)

An empirical colour scale in which 5 denotes absence of colour, 4 denotes a slight discolouration which is just noticeable and 3, 2, 1 and <1 denote progressively greater discolouration, was used for Table 4.

Table 4

| Stabiliser No. | Colour assessment according to scale 1 - 5 | | |
|---|---|---|---|
| | After incorporation | After exposure | Boiling water for 1 week |
| Without additive | 5 | 5 | 5 |
| 4 | 5 | 5 | 4-5 |
| 5 | 4-5 | 5 | 4-5 |
| 7 | 4-5 | 5 | 4-5 |
| 8 | 5 | 5 | 4-5 |
| 12 | 4-5 | 5 | 4-5 |
| 13 | 4-5 | 5 | 4-5 |
| 14 | 4-5 | 5 | 4-5 |

EXAMPLE 8

The test pieces described in Example 6 were tested for their colour stability, in particular:
(a) After incorporation (Table 5, column 2)
(b) After 500 hours' exposure in a Xenotest apparatus of Messrs. Hanau (Table 5, column 3)
(c) After treatment with boiling water for 1 week (Table 5, column 4).

An empirical colour scale in which 5 denotes absence of colour, 4 denotes a slight discolouration which is just noticeable and 3, 2, 1 and <1 denote progressively greater discolouration, was used for Table 5.

Table 5

| Stabiliser No. | Colour assessment according to scale 1 - 5 | | |
|---|---|---|---|
| | After incorporation | After exposure | Boiling water for 1 week |
| Without additive | 5 | 5 | 5 |
| 4 | 5 | 5 | 5 |
| 5 | 5 | 5 | 5 |
| 7 | 5 | 5 | 5 |
| 8 | 5 | 5 | 5 |
| 12 | 5 | 5 | 5 |
| 13 | 4-5 | 5 | 4-5 |
| 14 | 5 | 5 | 5 |

EXAMPLE 9

Shavings (chips) 25 μ thick are cut from the 1 mm thick test sheets described in Example 5 with the aid of a microtome. These chips are clamped between stainless steel grids and the sample carriers thus obtained are hung in a circulating air oven and are aged at 135° or at 147° C. The end point is defined as the time after which degraded polyproplylene falls out in a pulverised form if the grids are tapped gently (control 1 - 2 times daily). The results are quoted in hours (Table 6).

Table 6

| Stabiliser No. | Hours before decomposition begins | |
|---|---|---|
| | At 147° C | At 135° C |
| Without additive | 10 | 20 |
| 4 | 60 | 190 |
| 5 | 35 | 95 |
| 8 | 70 | 260 |
| 12 | 70 | 260 |
| 13 | 70 | 190 |
| 14 | 70 | 210 |

EXAMPLE 10

Shavings (chips) 25 μ thick are cut from the 1 mm thick test sheets described in Example 6 with the aid of a microtome. These chips are clamped between stainless steel grids and the sample carriers thus obtained are hung in a circulating air oven and are aged at 135° or at 147° C. The end point is defined as the time after which degraded polypropylene falls out in a pulverised form if the grids are tapped gently (control 1 - 2 times daily). The results are quoted in hours (Table 7).

Table 7

| Stabiliser No. | Hours before decomposition begins | |
|---|---|---|
| | At 147° C | At 135° C |
| Comparison | 10 | 20 |
| 4 | 120 | 380 |
| 5 | 45 | 140 |
| 8 | 40 | 166 |
| 12 | 90 | 330 |
| 13 | 120 | 260 |
| 14 | 70 | 190 |

EXAMPLE 11

Stabilisation of polyamide 6

100 parts of polyamide 6 granules (Perlon, unbleached, containing 1% of $TiO_2$, ex Glanzstoff A.G., relative viscosity of the 1% solution in concentrated sulphuric acid = 2.9) are mixed dry with 0.5 part of an additive listed in Table 8 which follows and are fused in a glass tube under nitrogen for 30 minutes at 270° C. Samples are taken from the melt reguli and are pressed at 260° C to give test films 0.3 mm thick. The films are subjected to an accelerated aging in a circulating air oven at 165° C. The degradation of the material is followed by periodically measuring the relative viscosity of a 1% strength solution in concentrated sulphuric acid. The time during which the relative viscosity falls to 1.7 from the initial value of 2.9 is determined as the end point (Table 8).

Table 8

| Stabiliser No. | Aging time. Decrease in the relative viscosity from 2.9 to 1.7 |
|---|---|
| Without stabiliser | 14 |
| 1 | 28 |
| 8 | 36 |

EXAMPLE 12

Protection of polyacrylonitrile (PAN) from yellowing 0.5 part of the stabiliser 1, together with 25 parts of PAN, are dissolved in 75 parts of dimethylformamide (DMF) at 70° C over the course of 4 hours. In visual comparison, the stabilised solution already shows a distinctly lighter colour than the additive-free solution. Films approx. 500 μ thick are spread from these solutions on a glass plate and are dried for 10 minutes at 125° C.

The degree of yellowing of the dried films is assessed visually on a white background, as follows:

Table 9

| | Discolouration |
|---|---|
| Comparison colour without additive | Yellow |
| 0.5% of stabiliser 1 | White with a very faint yellowish tinge |

The same results are obtained if instead of dimethylformamide other solvents such as, for example, ethylene carbonate-water mixture (80:20) are used.

EXAMPLE 13

Stabilisation of ABS 0.3% of stabiliser 1 is sprinkled onto unstabilised ABS resin and the sprinkled mixture is regranulated at 240° C on a single-screw extruder. For comparison, granules are prepared in the same way with no addition of stabiliser 1. The granules are injection-moulded into small sheets in the customary manner on an injection moulding machine at 250° C. The sheets are aged for 10 days in a circulating air oven at 80° C and the colour behaviour is assessed.

Table 10

| | Colour of the sheets | |
|---|---|---|
| | Initial condition | After 10 days at 80° C |
| Without stabiliser | Yellow-beige | Yellow-brownish |
| 0.23% of stabiliser 1 | Light beige | Light beige |

The addition of 0.3% of stabiliser 1 improves the colour of ABS in the initial condition and prevents discolouration during the oven aging process.

EXAMPLE 14

Stabilisation of ABS

Unstabilised ABS powder is mixed with 0.7% of stabiliser 1. The mixture is compounded and granulated in a Buss Co-kneader at 180° C. The granules are injection-moulded on a screw injection moulding machine (Ankerwerk Nurnberg/Ge) at 240° C to give small sheets of size 50 × 55 × 2 mm. The small sheets thus obtained are aged for 30 minutes in a circulating air oven at 200° C and their yellowing is assessed periodically (Yellowness Index according to ASTM D 1925-63T).

Table 11

| Stabiliser No. | 0 min. | 10 mins. | 15 mins. | 20 mins. | 30 mins. |
|---|---|---|---|---|---|
| None | 15.6 | 41.2 | 63.1 | 71.7 | 78.5 |
| 1 | 16.2 | 26.9 | 38.5 | 61.6 | 72.4 |

I claim:

1. A composition of matter comprising a poly monoolefin and 0.005 to 5% by weight of a compound of the formula $$\begin{array}{c} R_2 \quad R_1 \\ R_3 - \bigcirc - CH_2 - X - CH \begin{array}{c} S-R_6 \\ S-R_6 \end{array} \\ R_4 \quad R_5 \end{array}$$

in which $R_1$ and $R_5$ independently of one another are hydrogen or lower alkyl, one of $R_2$ and $R_3$ is hydroxyl and the other is alkyl, cycloalkyl or aralkyl, $R_4$ is hydrogen or, if $R_3$ is hydroxyl, also is alkyl, cycloalkyl or aralkyl, x is a group.

$$\begin{array}{c} R_8 \\ | \\ -C- \\ | \\ R_9 \end{array}$$

wherein $R_8$ is alkyl, aralkyl or phenyl and $R_9$ is alkyl, aralkyl, phenyl of the group $$-CH_2-\bigcirc\begin{array}{c} R_1 \quad R_2 \\ R_3 \\ R_5 \quad R_4 \end{array}$$

or $R_8$ and $R_9$ together are alkylene and $R_6$ is hydroxycarbonylalkyl, alkoxycarbonylalkyl, cycloalkoxycarbonylalkyl, aralkoxycarbonylalkyl or aryloxycarbonylalkyl.

2. The composition of claim 1 wherein the compound has the formula $$\begin{array}{c} \text{tert.Butyl} \\ HO-\bigcirc-CH_2-\underset{\underset{CH_3}{|}}{\overset{\overset{CH_3}{|}}{C}}-CH\begin{array}{c} S-CH_2-COOC_{18}H_{37} \\ S-CH_2-COOC_{18}H_{37} \end{array} \\ CH_3 \end{array}$$

3. The composition of claim 1 wherein the compound has the formula

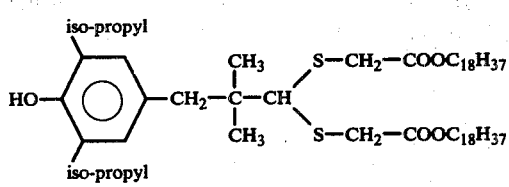

4. The composition of claim 1 wherein the compound has the formula

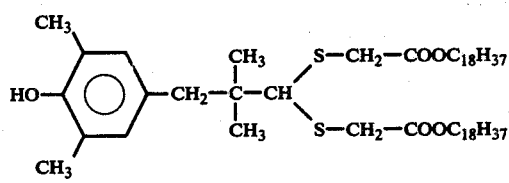

5. The composition of claim 1 wherein the compound has the formula

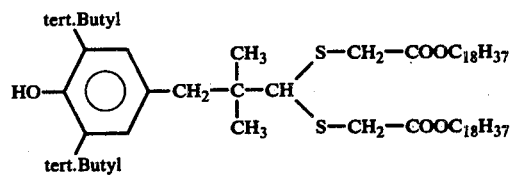

6. A composition of claim 1 wherein the polymer is polypropylene.

7. A composition of matter comprising polypropylene and 0.01 to 1.0% of a compound of claim 5.

8. The composition of claim 1, in which $R_1$ and $R_5$ independently of one another are hydrogen or methyl, one of $R_2$ and $R_3$ denotes hydroxyl and the other denotes alkyl having 1 to 8 carbon atoms, cycloalkyl having 6 to 8 carbon atoms or aralkyl having 7 to 9 carbon atoms, $R_4$ denotes hydrogen or, if $R_3$ denotes hydroxyl, additionally also denotes alkyl having 1 to 8 carbon atoms, cycloalkyl having 6 to 8 carbon atoms or aralkyl having 7 to 9 carbon atoms, x denotes a group

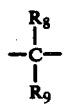

wherein $R_8$ is alkyl having 1 to 8 carbon atoms, aralkyl having 7 to 9 carboxyl atoms or phenyl, and $R_9$ denotes alkyl having 1 to 8 carbon atoms, aralkyl having 7 to 9 carbon atoms, phenyl or the group

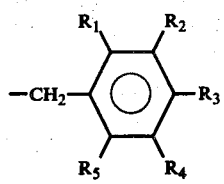

or conjointly with $R_8$, is alkylene having 2 to 11 carbon atoms and $R_6$ is hydroxycarbonylalkyl having 2 to 20 carbon atoms, alkoxycarbonylalkyl having 3 to 20 carbon atoms, cycloalkoxycarbonylalkyl having 7 to 10 carbon atoms, aralkoxycarbonylalkyl having 9 to 13 carbon atoms, phenoxycarbonylalkyl having 8 to 12 carbon atoms, alkylphenoxycarbonylalkyl having 9 to 16 carbon atoms, dialkylphenoxycarbonylalkyl having 10 to 16 carbon atoms, chlorophenoxycarbonylalkyl having 8 to 12 carbon atoms, or dichlorophenoxycarbonylalkyl having 8 to 12 carbon atoms.

9. The composition of claim 1, in which $R_1$ and $R_5$ independently of one another denote hydrogen or methyl, one of $R_2$ and $R_3$ denotes hydroxyl and the other denotes alkyl having 1 to 4 carbon atoms, $R_4$ denotes hydrogen or, if $R_3$ denotes hydroxyl, additionally also denotes alkyl having 1 to 4 carbon atoms, $R_8$ denotes alkyl having 1 to 4 carbon atoms or phenyl, $R_9$ denotes alkyl having 1 to 4 carbon atoms, phenyl or the group

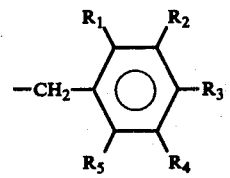

or together with $R_8$ denotes alkylene having 4 to 5 carbon atoms and $R_6$ denotes alkocycarbonylalkyl having 3 to 20 carbon atoms.

10. The composition of claim 1, in which $R_1$ and $R_5$ are hydrogen, $R_3$ is hydroxyl, $R_2$ denotes alkyl having from 1 to 4 carbon atoms, $R_4$ denotes alkyl having 3 to 4 carbon atoms, $R_8$ denotes alkyl having 1 to 4 carbon atoms, $R_9$ denotes alkyl having 1 to 4 carbon atoms or together with $R_8$ denotes pentamethylene and $R_6$ denotes alkoxycarbonylalkyl having 3 to 20 carbon atoms.

* * * * *

UNITED STATES PATENT AND TRADEMARK OFFICE
CERTIFICATE OF CORRECTION

PATENT NO. : 4,134,879
DATED : JANUARY 16, 1979
INVENTOR(S) : ANDREAS SCHMIDT

It is certified that error appears in the above-identified patent and that said Letters Patent are hereby corrected as shown below:

Related US Application data and Claim of Priority should be added to the front page of the Patent.

--Related U.S. Application Data

[60] Continuation of Serial No. 542,632, January 20, 1975, abandoned.

Foreign Application Priority Data

[30] January 21, 1974   CH   Switzerland.........787/74--

Signed and Sealed this

Ninth Day of June 1981

[SEAL]

Attest:

RENE D. TEGTMEYER

Attesting Officer    Acting Commissioner of Patents and Trademarks